United States Patent
Pearce et al.

(10) Patent No.: US 11,083,382 B2
(45) Date of Patent: *Aug. 10, 2021

(54) METHOD, INFORMATION PROCESSING APPARATUS AND SERVER FOR DETERMINING A PHYSIOLOGICAL PARAMETER OF AN INDIVIDUAL

(71) Applicant: XIM LIMITED, Southampton (GB)

(72) Inventors: Laurence Derek Pearce, Southampton (GB); Max Awan, Southampton (GB)

(73) Assignee: XIM LIMITED, Southampton (GB)

( * ) Notice: Subject to any disclaimer, the term of this patent is extended or adjusted under 35 U.S.C. 154(b) by 0 days.

This patent is subject to a terminal disclaimer.

(21) Appl. No.: 16/989,711

(22) Filed: Aug. 10, 2020

(65) Prior Publication Data

US 2020/0367772 A1    Nov. 26, 2020

Related U.S. Application Data

(63) Continuation of application No. 16/060,558, filed as application No. PCT/GB2016/053973 on Dec. 16, 2016, now Pat. No. 10,806,353.

(30) Foreign Application Priority Data

Dec. 18, 2015 (GB) ...................................... 1522406

(51) Int. Cl.
  *A61B 5/024* (2006.01)
  *G06T 7/90* (2017.01)
  (Continued)

(52) U.S. Cl.
  CPC ........ *A61B 5/02405* (2013.01); *A61B 5/0077* (2013.01); *A61B 5/024* (2013.01);
  (Continued)

(58) Field of Classification Search
  None
  See application file for complete search history.

(56) References Cited

U.S. PATENT DOCUMENTS

| 6,774,938 B1 | 8/2004 | Noguchi |
| 10,506,960 B2 | 12/2019 | Kaestle |

(Continued)

FOREIGN PATENT DOCUMENTS

| EP | 2774533 | 9/2014 |
| WO | 2013027027 | 2/2013 |

OTHER PUBLICATIONS

Feng, L. et al. "Motion artifacts suppression for remote imaging photoplethysmography", 2014 19th International Conference on Digital Signal Processing, IEEE, Aug. 20, 2014, pp. 18-23.

(Continued)

*Primary Examiner* — Kennedy Schaetzle
(74) *Attorney, Agent, or Firm* — Meunier Carlin & Curfman LLC

(57) ABSTRACT

An information processing apparatus is described. This determines a physiological parameter of an individual, the apparatus comprising: image circuitry configured to obtain a series of images of a skin exposed region of the individual; and processing circuitry configured to perform a periodogram on at least one of the red, green and blue channels of the skin exposed region of the series of images to obtain frequency components of the channel; and to determine the physiological parameter based on the periodogram.

15 Claims, 8 Drawing Sheets

(pulse measurement)

(51) Int. Cl.
    *G06T 7/00*         (2017.01)
    *A61B 5/103*       (2006.01)
    *A61B 5/08*         (2006.01)
    *A61B 5/1455*      (2006.01)
    *G16H 30/20*       (2018.01)
    *G16H 30/40*       (2018.01)
    *G16H 50/30*       (2018.01)
    *A61B 5/00*         (2006.01)
    *H04N 9/31*         (2006.01)
    *G16H 50/20*       (2018.01)

(52) U.S. Cl.
    CPC .......... *A61B 5/0816* (2013.01); *A61B 5/1032* (2013.01); *A61B 5/14551* (2013.01); *A61B 5/7225* (2013.01); *G06T 7/0012* (2013.01); *G06T 7/90* (2017.01); *G16H 30/20* (2018.01); *G16H 30/40* (2018.01); *G16H 50/30* (2018.01); *H04N 9/3182* (2013.01); *G06T 2207/10016* (2013.01); *G06T 2207/20056* (2013.01); *G06T 2207/20076* (2013.01); *G06T 2207/30088* (2013.01); *G06T 2207/30196* (2013.01); *G06T 2207/30201* (2013.01); *G06T 2207/30232* (2013.01); *G16H 50/20* (2018.01)

(56) References Cited

U.S. PATENT DOCUMENTS

| | | | |
|---|---|---|---|
| 10,806,353 B2 * | 10/2020 | Pearce | H04N 9/3182 |
| 2006/0247514 A1 | 11/2006 | Panasyuk et al. | |
| 2009/0290792 A1 | 11/2009 | Son | |
| 2010/0069758 A1 | 3/2010 | Barnes et al. | |
| 2011/0251493 A1 | 10/2011 | Poh et al. | |
| 2014/0275833 A1 | 9/2014 | Vanderpohl | |
| 2014/0378810 A1 | 12/2014 | Davis et al. | |
| 2015/0131879 A1 | 5/2015 | Lu et al. | |
| 2016/0007864 A1 | 1/2016 | Scharf et al. | |
| 2016/0361021 A1 | 12/2016 | Salehizadeh et al. | |
| 2017/0156608 A1 | 6/2017 | Mahar | |

OTHER PUBLICATIONS

Jiang, W. et al. "Real-time quantifying heart beat rate from facial video recording on a smart phone using kalman filters", 2014 IEEE 16th International Conference on E-Health Networking, Applications and Services (Healthcom), IEEE, Oct. 15, 2014, pp. 393-396.

International Search Report and Written Opinion dated Mar. 8, 2017, from International Application No. PCT/GB2016/053973, 12 pages.

Search Report under Section 17(5) dated May 31, 2016, from Application No. GB1522406.6, 4 pages.

Roald, N. "Estimation of Vital Signsfrom Ambient-Light Non-Contact PPG", Norwegian University of Science and Technology, Feb. 2013.

Kong, L. et al. "Non-Contact Detection of Oxygen Saturation based on Visible Light Imaging Device using Ambient Light", Apr. 29, 2013, vol. 21, No. 15, 8 pages.

Communication under Rule 71(3) EPC issued in EP 168163665, dated Jun. 5, 2020.

English Translation of Indian Examination report issued in IN 201847019602, dated Mar. 24, 2021, 5 pages.

* cited by examiner (pulse measurement)

(breathing measurement)

(HRV measurement)

(SP02 measurement)

| PHYSIOLOGICAL PARAMETERS | 3 | 2 | 1 | 0 | 1 | 2 | 3 |
|---|---|---|---|---|---|---|---|
| Respiration Rate | ≤8 | | 9 - 11 | 12 - 20 | | 21 - 24 | ≥25 |
| Oxygen Saturations | ≤91 | 92 - 93 | 94 - 95 | ≥96 | | | |
| Any Supplemental Oxygen | | Yes | | No | | | |
| Temperature | ≤35.0 | | 35.1-36.0 | 36.1-38.0 | 38.1-39.0 | ≥39.1 | |
| Systolic BP | ≤90 | 91 - 100 | 101 - 110 | 111 - 219 | | | ≥220 |
| Heart Rate | ≤40 | | 41 - 50 | 51 - 90 | 91 - 110 | 111 - 130 | ≥131 |
| Level of Consciousness | | | | A | | | V, P or U |

FIG. 7

METHOD, INFORMATION PROCESSING APPARATUS AND SERVER FOR DETERMINING A PHYSIOLOGICAL PARAMETER OF AN INDIVIDUAL

CROSS-REFERENCE TO RELATED APPLICATIONS

This application is a continuation of U.S. patent application Ser. No. 16/060,558, filed Jun. 8, 2018, now U.S. Pat. No. 10,806,353, which is a United States national phase application under 35 U.S.C. § 371 of International Application No. PCT/GB2016/053973, filed Dec. 16, 2016, which claims the benefit of priority to GB Application No. 1522406.6, filed Dec. 18, 2015, the contents of which are incorporated herein by reference in their entireties.

BACKGROUND

Field of the Disclosure

The present invention relates to a method, information processing apparatus and server for determining a physiological parameter of an individual.

Description of the Related Art

The "background" description provided herein is for the purpose of generally presenting the context of the disclosure. Work of the presently named inventors, to the extent it is described in the background section, as well as aspects of the description which may not otherwise qualify as prior art at the time of filing, am neither expressly or impliedly admitted as prior art against the present invention.

Over recent years, people have investigated methods of predicting an individual's health. Many of these techniques require the individual to be monitored for a period of time wearing a testing device. This is disadvantageous for at least two reasons. Firstly, this requires a person to remember that they should be tested and secondly, when they do remember, they have to wear the testing device.

Work has been carried out to partly automate this process. In WO2013/027027, a method of automatically monitoring an individual via a webcam is described. In this document, a person under test sits in front of the webcam and their pulse is identified from the slight variation in skin colour which occurs when the heart beats. The subject matter of WO2013/027027 is hereby incorporated by reference. However, the use of the system described in this document is likely to occur under artificial lighting. The system described in WO2013/027027 does address changes in ambient lighting. For example, the flickering of the light, which is invisible to the human eye, leads to errors in detecting the changes to skin colour. However, the system described in the prior art is quite complex and thus requires a large amount of processing power and calibration.

Further, the prior art system produced a noisy output. This leads to an erroneous pulse measurement.

It is an aim of embodiments of the present disclosure to address at least one of these problems.

SUMMARY

According to one embodiment, there is provided a method of determining a physiological parameter of an individual, the method comprising the steps of: obtaining a series of images of a skin exposed region of the individual; performing a periodogram on at least one of the red, green and blue channels of the skin exposed region of the series of images to obtain frequency components of the channel; and determining the physiological parameter based on the periodogram.

The method may further comprise performing band pass filtering on the periodogram.

The method may further comprise determining the power of each frequency component within the periodogram and determining the physiological parameter as the frequency component having the highest power within the periodogram.

The physiological parameter may be the frequency component having the highest power at or below a threshold power.

The band pass filtering may include a plurality of bands and the method further comprises: determining the number of frequency components within each of the bands and determining the physiological parameter based on the number of frequency components within each of the bands.

The physiological parameter may be a HRV and the HRV is calculated according to $$HRV = \frac{Number_{FirstFreq}}{Number_{SecondFreq}} \quad (1)$$

Where $Number_{FirstFreq}$ is the number of frequencies in a first frequency band and $Number_{SecondFreq}$ is the number of frequencies in a second frequency band, the frequency of the second frequency band being higher than the first frequency band.

According to another embodiment, an information processing apparatus for determining a physiological parameter of an individual, the apparatus comprising: image circuitry configured to obtain a series of images of a skin exposed region of the individual; and processing circuitry configured to perform a periodogram on at least one of the red, green and blue channels of the skin exposed region of the series of images to obtain frequency components of the channel; and to determine the physiological parameter based on the periodogram.

The apparatus may comprise band pass filter circuitry configured to perform band pass filtering on the periodogram.

The processing circuitry may be configured to determine the power of each frequency component within the periodogram and determine the physiological parameter as the frequency component having the highest power within the periodogram.

The physiological parameter may be the frequency component having the highest power at or below a threshold power.

The band pass filter circuitry may include a plurality of hands and the processing circuitry is further configured to determine the number of frequency components within each of the bands and determining the physiological parameter based on the number of frequency components within each of the bands.

The physiological parameter may be a HRV and the HRV is calculated according to $$HRV = \frac{Number_{FirstFreq}}{Number_{SecondFreq}} \quad (1)$$

Where $Number_{FirstFreq}$ is the number of frequencies in a first frequency band and $Number_{SecondFreq}$ is the number of frequencies in a second frequency band, the frequency of the second frequency band being higher than the first frequency band.

According to another embodiment, there is provided a server comprising communication circuitry and server processing circuitry configured to receive the physiological parameter from an information processing apparatus according to any one of the embodiments and in the event that the physiological parameter exceeds a threshold value, the server processing circuitry is configured to control the communication circuitry to issue an alert over a network.

According to another embodiment, there is provided a computer program comprising computer readable instructions which, when loaded onto a computer, configure the computer to perform a method according to any one of the embodiments.

The foregoing paragraphs have been provided by way of general introduction, and are not intended to limit the scope of the following claims. The described embodiments, together with further advantages, will be best understood by reference to the following detailed description taken in conjunction with the accompanying drawings.

BRIEF DESCRIPTION OF THE DRAWINGS

A more complete appreciation of the disclosure and many of the attendant advantages thereof will be readily obtained as the same becomes better understood by reference to the following detailed description when considered in connection with the accompanying drawings, wherein:

FIG. 7 shows a known Early Warning System developed by the Royal College of Physicians.

DESCRIPTION OF THE EMBODIMENTS

Figure 1:
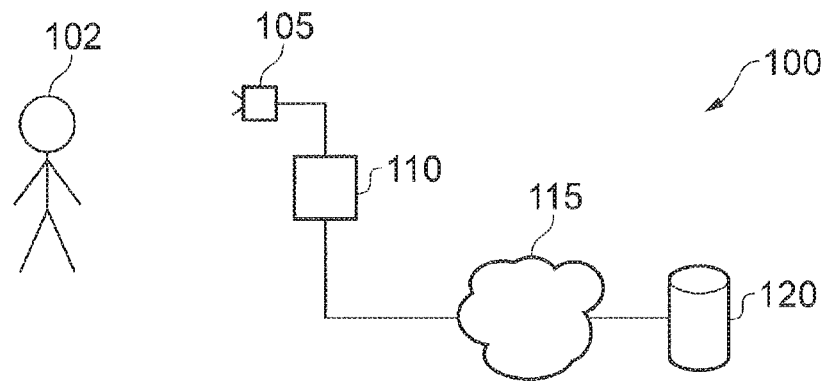
FIG. 1 describes a system according to one embodiment of the present disclosure.

Referring now to the drawings, wherein like reference numerals designate identical or corresponding parts throughout the several views.

Referring to FIG. 1, a system 100 according to one embodiment of the disclosure is shown. According to this embodiment there is provided a camera 105 that captures an image. In embodiments, the camera 105 is a webcam, although the disclosure is not so limited. For example, the camera 105 may be a video camera or a surveillance type camera, or alternatively may be a camera mounted in a telephone (smartphone) or a laptop computer. In embodiments, an individual 102 is located in front of the camera 105 and so the camera 105 is capturing an image for which a large proportion of the image is the individual. However, the camera 105 may instead capture a scene including one or more individuals.

The camera 105 feeds the captured image to an information processing device 110. The camera 105 may be connected to the information processing device 110 using a wired or wireless connection. This connection may be a point to point connection or may be over a network. Alternatively, the camera 105 may be integrated into the information processing device 110. This is particularly the case where the information processing device 110 is embodied as a telephone or laptop and the camera 105 is provided as part of the telephone or laptop.

The information processing device 110 is connected to the Internet 115. This connection may be over a network or the like. Within the Internet 115, a server 120 is provided. This server 120 contains a server storage device and a server processing device (neither are shown).

The functionality of the system 100 will become apparent later.

Figure 2:
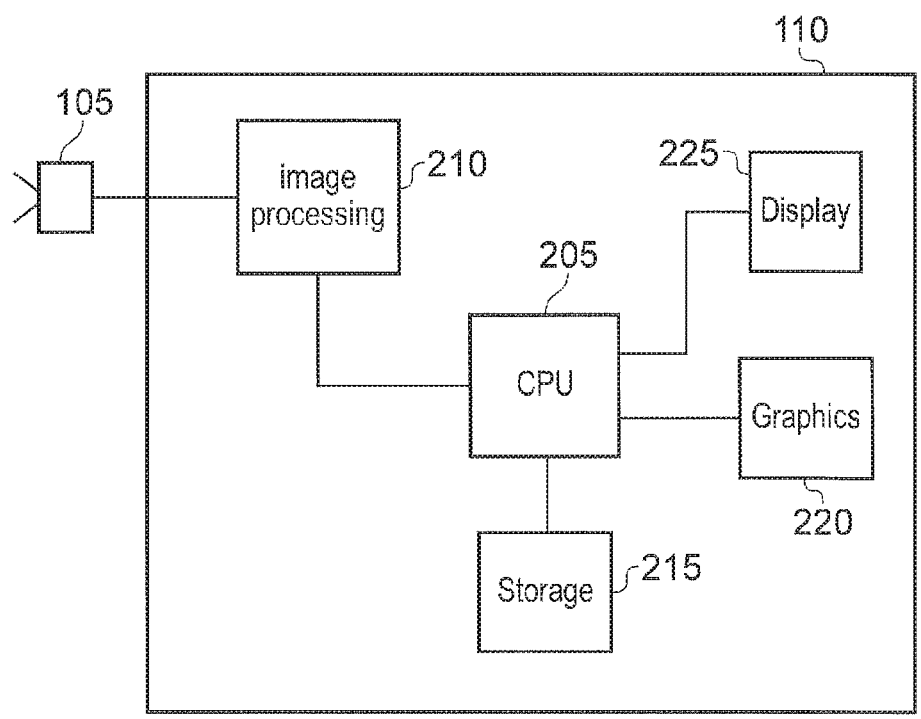
FIG. 2 describes an information processing device included in the system of FIG. 1.

Referring to FIG. 2, the information processing device 110 is shown in more detail. The information processing device 110 comprises an image processing device 210. The image captured by the camera 105 is fed into the image processing device 210. The image processing device 210 is connected to a central processing unit (CPU) 205 that controls the operation of the information processing device 110. The operation of the CPU is controlled by computer readable code stored on a storage unit 215 also connected to the CPU 205. The computer readable code comprises software instructions, which when read and performed by the CPU 205, controls the information processing device 110 to operate according to embodiments of the disclosure. As such, the storage unit 215 may be magnetically or optically readable storage medium. Alternatively, the storage unit 215 may contain solid-state type memory or the like.

Additionally connected to the CPU 205 are a display unit 225 and a graphics unit 220. The display unit 225 may be integrated into the information processing device 110 or may be separate to the information processing device 110. For example, in the case of the information processing device 110 being a telephone or laptop, the display unit 225 is likely to be integrated into the information processing device 110. However, in the case of the information processing device 110 being a desktop computer or the like, the display unit 225 is likely to be separate from the information processing device 110. The graphics unit 220 is a Graphics Processing Unit (GPU) that contains circuitry enabling efficient processing of images as would be appreciated.

Figures 3, 4:
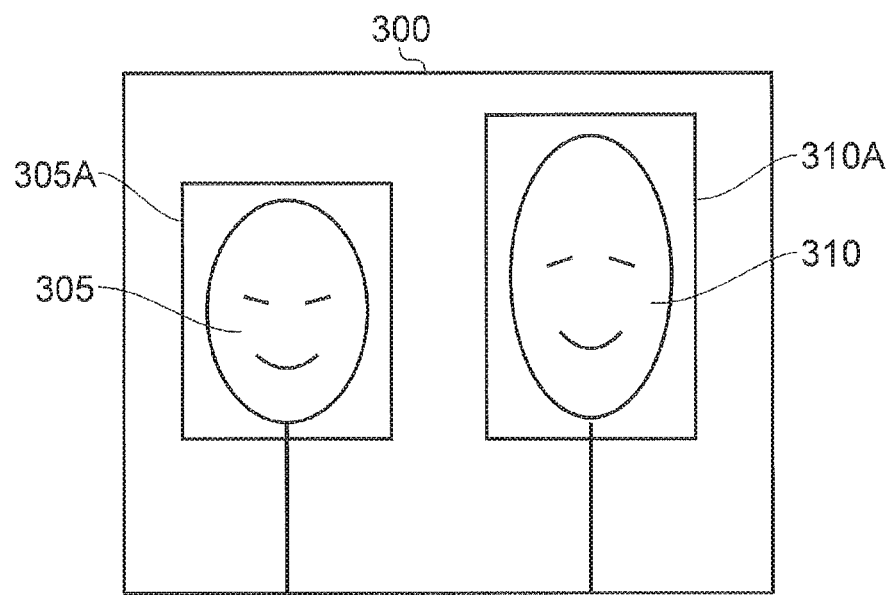
FIG. 3 describes face detection used in the information processing device of FIG. 1.
FIG. 4 describes a database showing a user's profile derived from embodiments of the present disclosure.

FIG. 3 shows an example of an image 300 captured by the camera 105. In the image 300, two individuals are shown. In embodiments of the present disclosure, the information processing device 110 detects the face of each individual in the image. This is because the colour changes within the face of the individual, and in particular the forehead of the individual, is currently believed to provide the best results for detecting the heart rate of the individual. This is explained in WO2013/027027 and so will not be described in any further detail for brevity. Additionally, as will be explained, the colour changes within the face can be used to derive other vital signs, such as breathing rate and Heart-Rate Variation (HRV). The mechanism to detect the vital signs will be described later.

The face of the first individual 305 is surrounded by first box 305A and the face of the second individual 310 is surrounded by second box 310A. The image contained within the first box 305A and the image contained within the second box 310A will be subsequently processed by the information processing device 110. This reduces the processing required to determine the heart rate as only the pertinent part of the image is processed. Moreover, after the face of the individual or individuals is detected in the image, the information processing device 110 may additionally perform object recognition and/or tracking. This known technique allows the information processing device 110 in this embodiment to associate the heart rate that has been detected with the individual. This is useful where, as in this case, the image contains two or more individuals. In other words, using object detection and recognition, the heart rate of two or more individuals may be determined simultaneously. This allows the camera 105 to capture a scene such as a common room within an elderly residence where a number of elderly people congregate. The information processing device 110 then captures the image, detects the face of each elderly resident and recognises the resident so that their heart rate can be monitored and their profile updated.

FIG. 4 shows a table containing the vital signs captured using the system. As is seen in FIG. 4, the vital signs for two individuals (Edna and Tony) are shown in the table. Of course, the number of individuals is completely scalable to more or fewer individuals. Additionally, the table contains the vital signs (pulse, breathing rate and HRV) at consecutive moments in time. This enables trends within the individual's vital signs to be monitored automatically. For example, if during the course of a short period of time, the individual's pulse rate increases by 20%, this may indicate a problem. However, if the individual has a relatively low resting pulse, then an increase of 20%, if taken in isolation, may not be regarded as a problem. This ability to observe trends over a period of time is useful because the vital signs at any point in time are comparable to the normal resting vital signs of that individual rather than an arbitrary general figure. This allows for better vital signs analysis for an individual.

Figure 5:
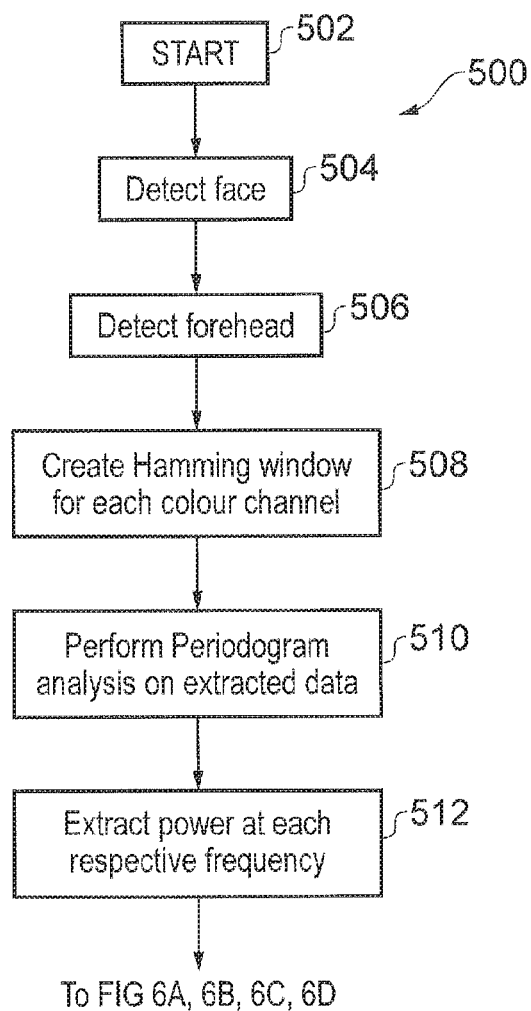
FIG. 5 describes a flow chart according to one embodiment of the present disclosure.

Referring to FIG. 5, a flowchart 500 explaining the operation of an embodiment of the disclosure is shown. The operation starts at step 502 when a frame of an image is captured. In this operation, the camera 105 captures a frame of an image and the image is passed to the information processing device 110. The image processing device 110 then performs processing on the frame of the image to detect any faces within the image. Specifically, the image processing unit 210 processes the image to detect any faces within the image. The image processing unit 210 may additionally perform object recognition on the detected faces to identify specific individuals within the image. The image processing unit 210 then identifies each individual's forehead in the image using known techniques such as that explained in https://github.com/thearn/webcam-pulse-detector. The content of this webpage is incorporated herein by reference. This is step 506.

The image processing unit 210, under control of the CPU 205, performs a known Independent Component Analysis on the detected individual's forehead. The ICA is performed to remove noise from the captured frame of the image.

Further, in embodiments, the noise may be categorised into a number of categories. In [1], four noise sources are categorised. These are mechanical noise, white noise, Gaussian Noise and other (or unknown) sources. In [1], various techniques are applied to deal with each of these sources.

In embodiments, however, further noise sources not envisaged in [1] are categorised.

Specifically, ambient lighting noise is detected and reduced as follows: Ambient lighting noise can be periodic such as sub-harmonics of artificial lighting flicker, or aperiodic such as sudden power dropouts. Periodic noise can be detected as waveforms with amplitudes higher than would be expected from the physiological signals sought. Periodic noise can be filtered by removing signals with frequencies outside of expected range and those with amplitude above a empirically determined threshold. Aperiodic noise can be detected as sudden changes in white balance and mitigated in the same way as mechanical artefacts described below.

Moreover, the techniques used for detecting mechanical noise in [1] are different to the present disclosure. In the present disclosure, the white balance data associated with each frame is captured from the camera 105. The inventors have identified that when sudden changes occur in white balance between consecutive frames or frames over a pre-determined time frame then mechanical noise exists. In embodiments, the inventors have identified that when the white balance for the overall image changes by 20% over a period of 5 frames, then some form of mechanical noise exists. One example of mechanical noise is a sudden movement of a user's face.

For each frame, where mechanical noise is identified using the above method, the sample values derived from the affected images are not used in further analysis. By discarding the sample values derived from the captured images where mechanical noise has been detected by white balance change as described, the accuracy of the average measured characteristics of the user over a sampling period of more than 30 seconds is improved.

When the mechanical noise is below the threshold so the captured image is used in further analysis, this captured image is then separated into its constituent Red, Green and Blue (R, G, B) signals. The process then moves to step 508 where a Hamming window is created for each colour channel in a number of captured images of the individual's forehead. In other words, the Hamming Window is created for each of the R, G and B signals, and number of samples, over a period of time. This period of time may be 10 seconds, or 15 seconds, or 30 seconds or any appropriate period. Additionally, although a Hamming Window is specifically noted, the disclosure is not limited and any windowing function may be used. This known technique allows for a section of the continuous R, G, B signals to be processed.

One further type of noise is jitter noise. Jitter noise is temporal distortion where a host device (such as the image processing device 110) processes at a varying frame rate. For example, in periods of heavy processing, the image processing device 110 may not process the captured images at the same rate as during periods where the image processing device is operating under less heavy processing. In order to reduce this jitter noise, a timestamp may be recorded with each image. The time stamp indicates the time at which the image is captured. Prior to further processing, the captured images can be resampled to ensure that the signals to be analysed feature a constant sample rate.

In WO 20131027027 and the technique described in https://github.com/thearn/webcam-pulse-detector, a Fast Fourier Transform (FFT) is used convert the R, G, B signal into its frequency components for later processing. However, when an individual's skin colour is captured, the use of artificial lights flickering at a high frequency (such as 50 Hz) produces noise, and means that the subsequent measurement of the heart rate can be erroneous. This is because the lighting applied to the individual's forehead changes between consecutive frames. One of the artefacts of this kind of noise can be loss of regular samples. In order to correct for this, a periodogram is calculated instead of the FFT described in WO 2013/027027.

Specifically, in embodiments, a Lomb-Scargle Periodogram is calculated. The inventors found that the loss of regular samples caused irregularly sampled data. The use of the periodogram, and especially the Lomb-Scargle Periodogram is more effective at finding periodicity in irregularly-sampled data than the known FFT mechanism which assumes regularly sampled data. This is step 510.

The output from the periodogram analysis is a set of frequency components of each of the R, G and B signals for the region of interest over the period determined by the Hamming Window. The power of each frequency component is then calculated in stop 512 using a known technique. Thus, the output of step 512 is a two dimensional data set with all the frequencies contained within each of the R, G and B signals over the period and their respective power.

Of course, although the foregoing describes performing the periodogram analysis on each of the R, G and B channels, the disclosure is not so limited. For example, the periodogram analysis may be performed on one or more of the R, G, B channels instead.

In other embodiments, the Hue-Saturation-Value (HSV) colour domain channels for each image may be used in the process of FIG. 5. In this instance, the forehead is detected in step 506 of FIG. 5 with the associated noise reduction applied. However, instead of separating the image into constituent red, green and blue components, the HSV colour domain components are derived.

Figure 6A:
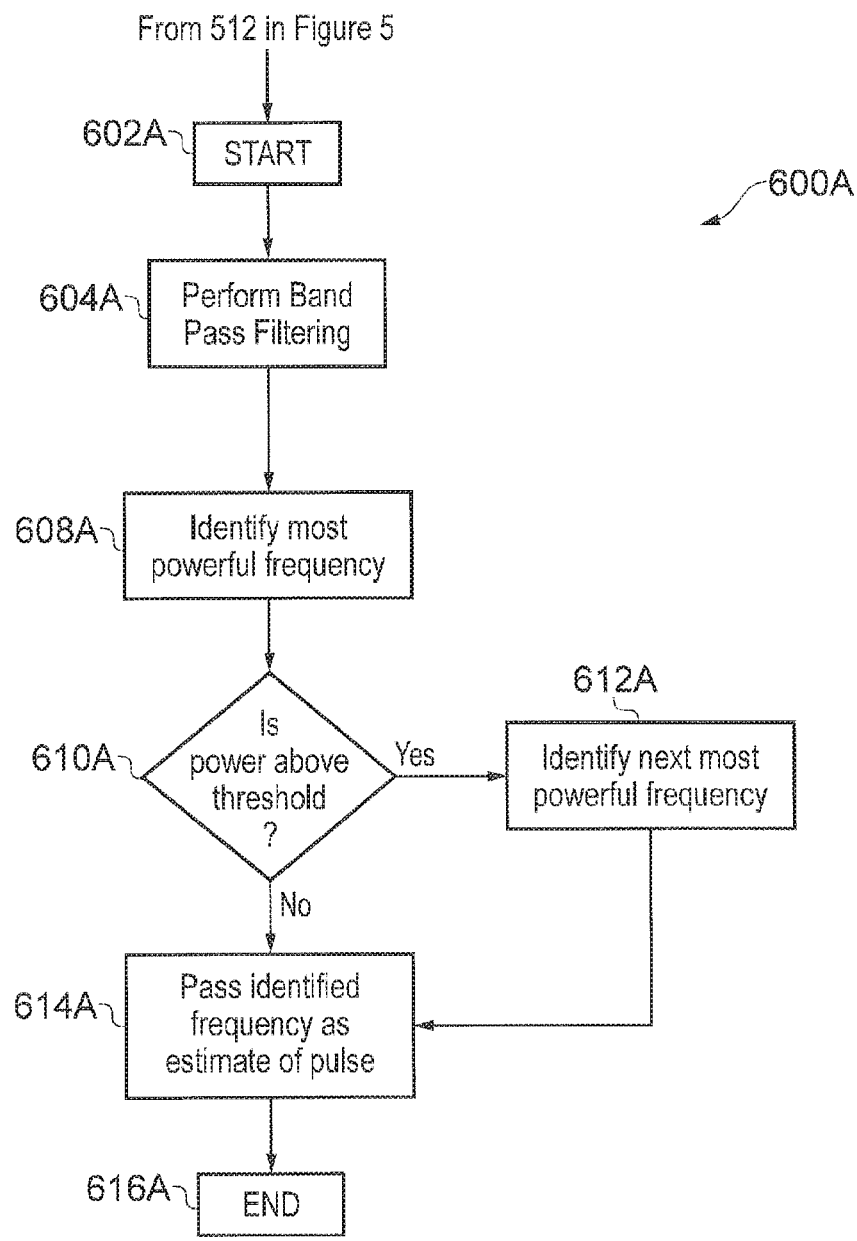
FIG. 6A describes a flow chart according to embodiments of the present disclosure for establishing pulse measurement.

Referring to FIG. 6A, a flowchart 600A describing the measurement of the individual's pulse is shown. The output of step 512 is fed into the start phase 602A of the flowchart 600A. The output of step 512 (which is a two dimensional data set with all the frequencies contained within each of the R, G and B signals over the period and their respective power) is applied to a band pass filter. The band pass filter has a pass range of 0.7 to 3 Hz. The frequency range of the band pass filter is selected to pass through typical frequencies of pulse. The purpose of the band pass filter therefore is to remove any harmonics or spurious high or low frequency components (e.g. from head movement, flickering light sources or reflections) which could produce erroneous results. The band pass filter is applied to each of the R, G, B colour channels. The band pass filtering occurs at step 604A. In the instance of the HSV colour domain channels being used instead of the R, G, B values, the band pass filtering step is carried out using a $5^{th}$ order Butterworth filter to remove the low and high frequency components.

In step 608A, the frequency component having the highest power for each of the R, G and B (or HSV) channels is identified.

The process moves onto step 610A, where the power level of the highest power frequency component is compared with a threshold. In embodiments, the threshold of the power spectral density is 20. This is because the pulse is detected using slight skin colour changes on the individual's face. As these are only slight skin colour variations, any very large power frequency components will be due to artificial artefacts such as shadows or lighting changes that cause much higher variations in colour in the image.

In the case that the highest power frequency level is above the threshold, the "yes" path is followed to step 612A. At step 612A, the next highest power frequency level is identified. Although not shown in FIG. 6A, this next highest power level is compared against the threshold. In the event that the next highest power level is above the threshold, the next highest power level is identified and so on until the highest power level at or under the threshold is identified. Then the process moves to step 614A.

In the case that the highest power frequency level is at or below the threshold value, the process also moves to step 614A. The frequency having the highest power level is determined to be the value of the pulse of the individual. This value is passed, along with an identifier which uniquely identifies each individual, to the server 120 for storage in the table shown in FIG. 4. In addition to the identifier, a timestamp is sent so that the moment the measurements were captured is recorded in the table. It is of course possible for the server 120 to apply the timestamp when the measurements are received. However, in the event that the server 120 is offline or them is a backlog of measurements to be recorded, then the synchronisation between the measurements and the timestamp recorded will be lost.

After the server 120 has acknowledged receipt of the measurements, then the process ends at step 616A.

Figure 6B:
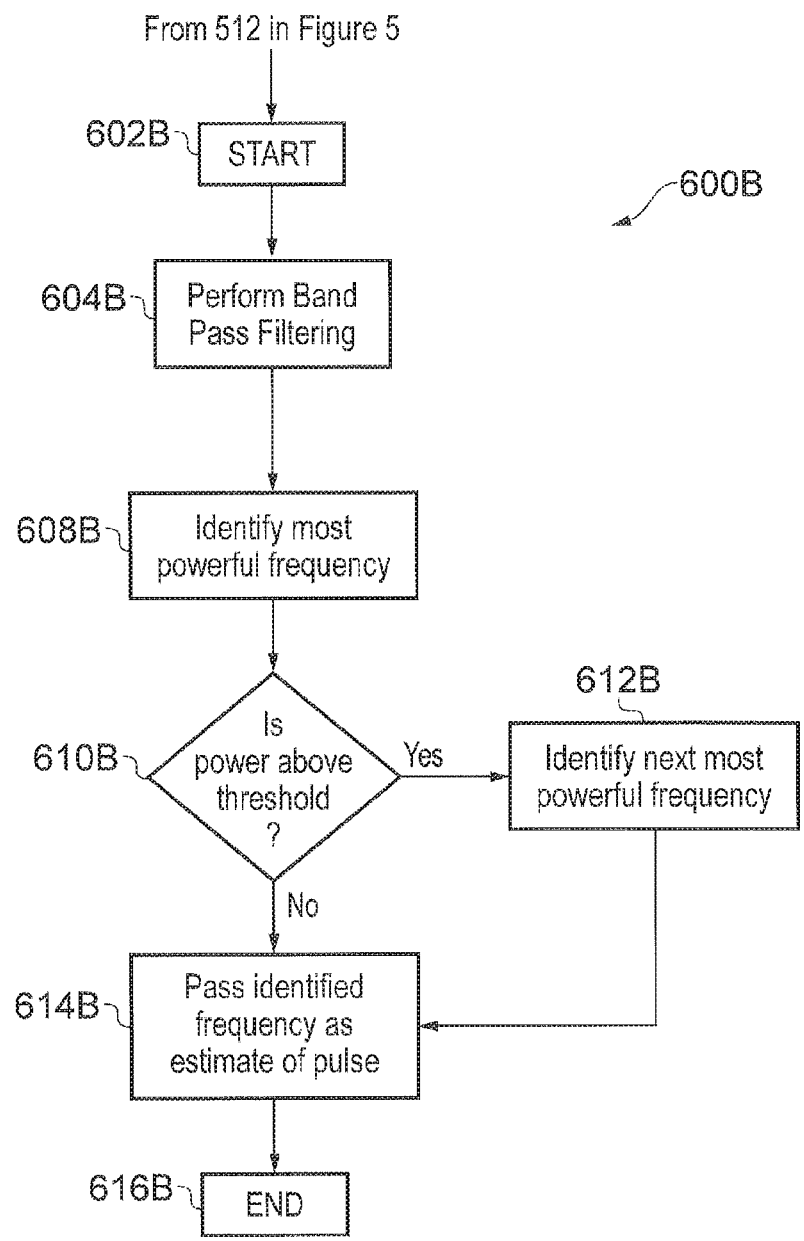
FIG. 6B describes a flow chart according to embodiments of the present disclosure for establishing breathing measurement.

Referring to FIG. 6B, a flowchart 600B describing the measurement of the individual's breathing rate is shown. The output of step 512 (which is a two dimensional data set with all the frequencies contained within each of the R, G and B signals over the period and their respective power) is fed into the start phase 602B of the flowchart 600B. The output of step 512 is applied to a band pass filter. The band pass filter has a pass range of 0.1 Hz to 0.5 Hz. The frequency range of the band pass filter is selected to pass through typical frequencies of breathing rates. This purpose of the band pass filter therefore is to remove any harmonics or spurious high or low frequency components which could produce erroneous results.

The band pass filter is applied to each of the R, G, B colour channels. The band pass filtering occurs at step 604B. As in FIG. 6A, in the instance of the HSV colour domain channels being used instead of the R, G, B values, the band pass filtering step is carried out using a $5^{th}$ order Butterworth filter to remove the low and high frequency components.

In step 608B, the frequency component having the highest power for each of the R, G and B (or HSV) channels is identified.

The process moves onto step 610B, where the power level of the highest power frequency component is compared with a threshold. In embodiments, the threshold of the power spectral density is 10. This is because the breathing is detected using slight skin colour changes on the individual's face. As these are only slight skin colour variations, any very large power frequency components will be due to artificial artefacts such as shadows or light flicker that cause much higher variations in colour in the image.

In the case that the highest power frequency level is above the threshold, the "yes" path is followed to step 612B. At step 612B, the next highest power frequency level is identified. Although not shown in FIG. 6B, this next highest power level is compared against the threshold. In the event that the next highest power level is above the threshold, the next highest power level is identified and so on until the highest power level at or under the threshold is identified. Then the process moves to step 614B.

In the case that the highest power frequency level is at or below the threshold value, the "no" path is followed and the process also moves to step 614B. The frequency having the highest power level is determined to be the value of the breathing rate of the individual. This value is passed, along with an identifier which uniquely identifies each individual, to the server 120 for storage in the table shown in FIG. 4. In addition to the identifier, a timestamp is sent so that the moment the measurements were captured is recorded in the table. It is of course possible for the server 120 to apply the timestamp when the measurements are received. However, in the event that the server 120 is offline or there is a backlog of measurements to be recorded, then the synchronisation between the measurements and the time recording will be lost.

After the server 120 has acknowledged receipt of the measurements, then the process ends at step 616B.

Figure 6C:
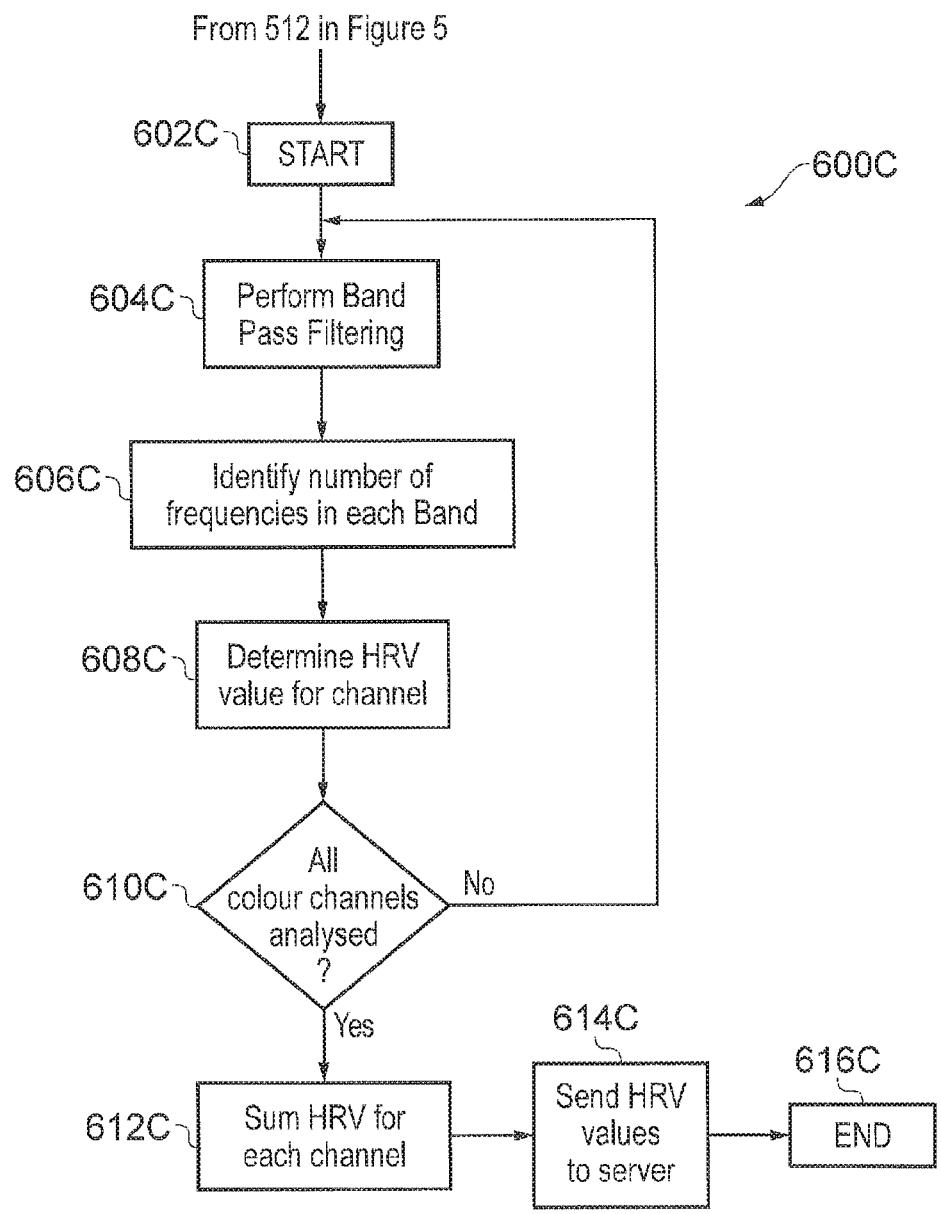
FIG. 6C describes a flow chart according to embodiments of the present disclosure for establishing HRV measurement.

Referring to FIG. 6C, a flowchart 600C showing the calculation of Heart Rate Variability (HRV) is described. The process starts at step 602C where the output of step 512 (which is a two dimensional data set with all the frequencies contained within each of the R, G and B signals over the period and their respective power) is provided. The process then moves to step 604C where band-pass filtering is performed. In this case, the band-pass filters have the range 0 to 0.04 Hz to extract very low frequencies; 0.04 to 0.15 Hz to extract low frequencies and 0.15 to 0.4 Hz to extract high frequencies. This band pass filtering is carried out on each of the red, green and blue channels. In the instance of the HSV colour domain channels being used instead of the R, G, B values, the band pass filtering step is carried out using a $5^{th}$ order Butterworth filter to remove the low and high frequency components.

The process then moves to step 606C where the number of frequencies in each of the extracted bands are counted. Again this is done for each colour channel. It is important to note here that for HRV, the number of frequencies within each band is important rather than the power of each frequency.

The process then moves to step 608C whom the HRV for each colour channel is calculated. The value of HRV is calculated using equation 1 below:

$$HRV = \frac{Number_{LowFreq}}{Number_{HighFreq}} \quad (1)$$

Where $Number_{LowFreq}$ is the number of frequencies in the low frequency band and $Number_{HighFreq}$ is the number of frequencies in the high frequency band.

The process then moves to step 610C where a check is made to ensure that all colour channels have been analysed. In the event that not all of the channels have been analysed, the "no" path is followed and the process returns to step 604C and one other channel is analysed. Alternatively, if all the colour channels have been analysed, the process follows the "yes" path to step 612C.

In step 612C, the HRV values for each of the channels are summed. This summed value is sent to the server 120 as the measured HRV value for the individual in step 614C. In addition, or alternatively, the HRV values for each individual channel may be sent to the server 120. In other words, although the foregoing describes the summed value of HRV being sent to the server 120 to update the table in FIG. 4, the disclosure is not limited to this and the HRV value for the red channel, the HRV value for the green channel and the HRV value for the blue channel may be sent to the server 120.

The process ends in step 616C.

In [2], two webcameras with optical filters were used to measure the Oxygen Saturation Levels SPO2 levels.

In [2], the value of SPO2 is measured as a ratio, R calculated below:

$R=(AC(Red)/DC(Red))/(AC(Green)/DC(Green))$.

The Oxygen saturation, SPO2 is then calculated as
SPO2=a−bR, where a and b are empirical coefficients determined by calibration as explained in [2].

Two narrow colour frequencies are used where at one, absorption coefficients HbO2 and Hb are very different while at the other they are very close. Known oximeters use 660 nm (Red) and 940 nm (IR). However, no power in each R, G, B component is observed in reflected IR as this is outside the colour space of known webcameras. Additionally, in [2] a large variance in absorption coefficients is observed at 660 nm, and a narrow variance at 520 nm. Therefore, the absorption coefficients at 660 nm and 520 nm are used in [2].

However, in [2], two webcameras are required with optical filters; one tilter set at 660 nm and a second optical filter set at 520 nm.

Figure 6D:
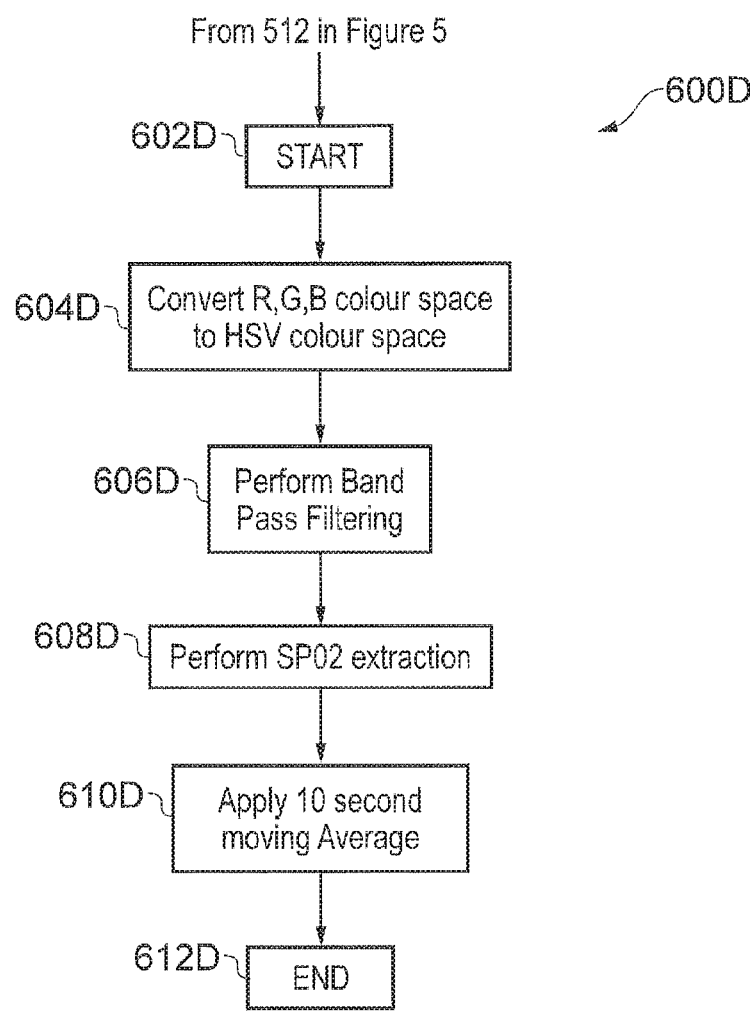
FIG. 6D describes a flow chart according to embodiments of the present disclosure for establishing SPO2 measurement.

Instead, as shown in FIG. 6D, in embodiments of the present disclosure, the process 600D associated with SPO2 measurement, starts at step 602D. The R, G, B camera signal from step 512 of FIG. 5 is converted to the HSV colour space in step 604D. The images are then narrowly filtered closely around light wavelengths (520 nm and 660 nm). Bandpass filtering of the HSV colour space signals occurs in step 606D. Specifically, a 0.7 Hz-3.0 Hz band pass filter is applied to the HSV colour space signal in step 606D.

SPO2 extraction is performed in step 608D.

The extracted SPO2 signal is applied to a 10 second moving average in step 610D. This smooths variations during each cardiac cycle. The process ends in step 612D.

The calculated parameters can be used to estimate the individual's blood pressure. Specifically, further analysis of the captured signals permit an estimation of systolic and diastolic blood pressure to be determined by one of two methods. The first method can provide an estimation derived from heart rate using a formula based on the subject's age, gender, weight and height. This method consists of firstly calculating the body surface area (BSA) of the user using a known technique such as the DuBois formula explained in https://en.wikipedia.org/wiki/Body_surface_area#Calculation.

$BSA=0.007184 \times W^{0.425} \times H^{0.725}$ \hfill Equation (1)

Ejection Time (ET) is then estimated assuming that the subject is seated as follows:

ET=386−1.64HR \hfill Equation (2)

Using a set of empirically calculated coefficients (a-f) Stroke Volume (SV) is derived from the heart rate (HR) from the process of FIG. 6A, BSA, ET and the user's age (A) in years. This is equation (3) below.

SV=a−b(ET−c)−dHR+eBSA−fA \hfill Equation (3)

Pulse Pressure (PP) is then estimated with further empirically calculated coefficients g, h, i, j as Equation (4) below.

PP=|SV/(gW−hA−iHR+j)| \hfill Equation(4)

Mean Pulse Pressure (MPP) is calculated as QVR, where Q is derived from one of 2 coefficients dependent on the user's gender and vascular resistance (VR) is a broad population average of 18.31.

Then Systolic Pressure is calculated as SP=MPP+(k/lPP) where k and l are empirically calculated.

And Diastolic Pressure is calculated as DP=MPP−PP/3

An example of this estimation can be found at https://github.com/danialgoodwin/android-app-contactless-vital-signs.

The second method consists of taking two pulse signals from separate parts of the body and comparing them in order to calculate the pulse transmit time (pulse wave velocity) through the arterial system. Blood pressure can then be estimated using a method as described at http://link.springer.com/chapter/10.1007%2F978-3-540-36841-0_144.

The contents of both of these websites, insofar as they describe two methods of measuring blood pressure, are hereby incorporated by reference.

Within the server 120, the content of the generated table is analysed. Specifically, the content of the generated table is compared to the Early Warning Score which has been developed by the Royal College of Physicians in the United Kingdom. A diagram showing the Early Warning Score is provided in FIG. 7. The purpose of the Early Warning Score currently is to provide a monitor for patients who present in hospitals with acute illness. The physiological parameters, respiratory rate, oxygen saturations, temperature, systolic blood pressure, pulse rate and level of consciousness are monitored. A score is then applied to each parameter as it is measured. The value of the score reflects how extreme the parameter is from the normal parameter. The score is then aggregated and if the aggregated score is too high (i.e. above a threshold), the patient is in need of urgent medical treatment. In the known implementation of the Early Warning System, trained staff need to periodically and regularly measure these physiological parameters.

However, using the system of the disclosure, the individual is monitored and the server 120 issues an alert to a monitoring station (not shown) over the Internet. The server 120 will issue the alert and will identify the individual with the aggregated score that is above the threshold. The monitoring station will alert the trained member of staff to indicate that an alert has been issued, and the identity and possibly current location of the individual. The trained member of staff can then visit the individual to apply medical aid. By automatically monitoring patients using the presently described system, it is possible to re-assign trained staff to other duties whilst still monitoring the patients Although the above mentions that the aggregated score is calculated, the disclosure is not so limited. In fact, it is possible that if the score of any one or any particular one of the physiological parameters is above a threshold score, then the alert will be issued. It is envisaged that the alert will also include the parameter that has exceeded the score, as well as the value of that physiological parameter. This will assist the trained member of staff in providing medical aid.

In order to monitor the thresholds, a Complex Event Processor is set up to monitor each of the physiological parameters (including the aggregate value) and to issue the alert should one of the parameters, or the aggregate of the parameters exceeds a threshold value.

Further, although the Early Warning Score has been described with reference to medical care, the disclosure is not so limited. The monitoring system may be provided in care homes, such as elderly residential care, where the individuals within the home have higher than average medical care needs. In this instance, the monitoring station may be located in the home.

Further, although the foregoing has described the physiological parameters as being relevant to the Early Warning System, the disclosure is not so limited. Specifically, the monitored parameters may be used to detect higher than average levels of stress or other medical conditions.

Although the foregoing has been described with the server receiving the physiological parameter, the disclosure is not so limited. It is envisaged that the server may receive the image prior to analysis and the server may perform the analysis to determine the physiological parameter. Indeed the processing may be distributed between the information processing apparatus and the server in any suitable manner as would be appreciated.

Obviously, numerous modifications and variations of the present disclosure are possible in light of the above teachings. It is therefore to be understood that within the scope of the appended claims, the disclosure may be practiced otherwise than as specifically described herein.

In so far as embodiments of the disclosure have been described as being implemented, at least in part, by software-controlled data processing apparatus, it will be appreciated that a non-transitory machine-readable medium carrying such software, such as an optical disk, a magnetic disk, semiconductor memory or the like, is also considered to represent an embodiment of the present disclosure.

It will be appreciated that the above description for clarity has described embodiments with reference to different functional units, circuitry and/or processors. However, it will be apparent that any suitable distribution of functionality between different functional units, circuitry and/or processors may be used without detracting from the embodiments.

Described embodiments may be implemented in any suitable form including hardware, software, firmware or any combination of these. Described embodiments may optionally be implemented at least partly as computer software running on one or more data processors and/or digital signal processors. The elements and components of any embodiment may be physically, functionally and logically implemented in any suitable way. Indeed the functionality may be implemented in a single unit, in a plurality of units or as part of other functional units. As such, the disclosed embodiments may be implemented in a single unit or may be physically and functionally distributed between different units, circuitry and/or processors.

Although the present disclosure has been described in connection with some embodiments, it is not intended to be limited to the specific form set forth herein. Additionally, although a feature may appear to be described in connection with particular embodiments, one skilled in the art would recognize that various features of the described embodiments may be combined in any manner suitable to implement the technique.

Embodiments of the present disclosure can be described in the following numbered paragraphs.

1. A method of determining a physiological parameter of an individual, the method comprising the steps of obtaining a series of images of a skin exposed region of the individual; performing a periodogram on at least one of the red, green and blue channels of the skin exposed region of the series of images to obtain frequency components of the channel; and determining the physiological parameter based on the periodogram.

2. A method according to paragraph 1, further comprising performing band pass filtering on the periodogram.

3. A method according to paragraph 2, further comprising determining the power of each frequency component within the periodogram and determining the physiological parameter as the frequency component having the highest power within the periodogram.

4. A method according to paragraph 3, wherein the physiological parameter is the frequency component having the highest power at or below a threshold power.
5. A method according to paragraph 2, wherein the band pass filtering includes a plurality of bands and the method further comprises: determining the number of frequency components within each of the bands and determining the physiological parameter based on the number of frequency components within each of the bands.
6. A method according to paragraph 5, wherein the physiological parameter is a HRV and the HRV is calculated according to $$HRV = \frac{Number_{FirstFreq}}{Number_{SecondFreq}} \quad (1)$$

Where $Number_{FirstFreq}$ is the number of frequencies in a first frequency band and $Number_{SecondFreq}$ is the number of frequencies in a second frequency band, the frequency of the second frequency band being higher than the first frequency band.
7. A method according to paragraph 1, comprising applying a timestamp to each image in the series of images and providing a constant sample rate of images based on the applied timestamp.
8. A method according to paragraph 2 comprising converting each of the R, G, B signals into a Hue-Saturation-Value prior to the band-pass filtering.
9. A method according to paragraph 8 comprising calculating the SPO2 value according to:
SPO2=a−bR, where a and b are empirical coefficients determined by calibration and R=(AC(Red)/DC(Red))/(AC(Green)/DC(Green)).
10. A method according to paragraph 1, comprising capturing the white balance of each image in the series, and in the event that the difference in white balance between two images in the series is above a threshold, the method comprises ignoring the RGB mean values calculated from the affected image.
11. A method according to paragraph 7, comprising capturing the white balance of each image in the series, and in the event that the difference in white balance between two images in the series is above a threshold, the method comprises ignoring the HSV mean values calculated from the affected image
12. An information processing apparatus for determining a physiological parameter of an individual, the apparatus comprising: image circuitry configured to obtain a series of images of a skin exposed region of the individual; and processing circuitry configured to perform a periodogram on at least one of the red, green and blue channels of the skin exposed region of the series of images to obtain frequency components of the channel; and to determine the physiological parameter based on the periodogram.
13. An apparatus according to paragraph 12, further comprising band pass filter circuitry configured to perform band pass filtering on the periodogram.
14. An apparatus according to paragraph 13, wherein the processing circuitry is configured to determine the power of each frequency component within the periodogram and determine the physiological parameter as the frequency component having the highest power within the periodogram.
15. An apparatus according to paragraph 14, wherein the physiological parameter is the frequency component having the highest power at or below a threshold power.
16. An apparatus according to paragraph 13, wherein the band pass filter circuitry includes a plurality of bands and the processing circuitry is further configured to determine the number of frequency components within each of the bands and determining the physiological parameter based on the number of frequency components within each of the bands.
17. An apparatus according to paragraph 16, wherein the physiological parameter is a HRV and the HRV is calculated according to $$HRV = \frac{Number_{FirstFreq}}{Number_{SecondFreq}} \quad (1)$$

Where $Number_{FirstFreq}$ is the number of frequencies in a first frequency band and $Number_{SecondFreq}$ is the number of frequencies in a second frequency band, the frequency of the second frequency hand being higher than the first frequency band.
18. An apparatus according to paragraph 12, wherein the processing circuitry is configured to apply a timestamp to each image in the series of images and providing a constant sample rate of images based on the applied timestamp.
19. An apparatus according to paragraph 13 wherein the image processing circuitry is configured to convert each of the R, G, B signals into a Hue-Saturation-Value prior to the band-pass filtering.
20. An apparatus according to paragraph 19 wherein the processing circuitry is configured to calculate the SPO2 value according to:
SPO2=a−bR, where a and b are empirical coefficients determined by calibration and R=(AC(Red)/DC(Red))/(AC(Green)/DC(Green)).
21. An apparatus according to paragraph 12, wherein the processing circuitry is configured to capture the white balance of each image in the series, and in the event that the difference in white balance between two images in the series is above a threshold, and to ignore the RGB mean values calculated from the affected image.
22. An apparatus according to paragraph 18, wherein the processing circuitry is configure to capture the white balance of each image in the series, and in the event that the difference in white balance between two images in the series is above a threshold, and ignore the HSV mean values calculated from the affected image
23. A saver comprising communication circuitry and server processing circuitry configured to receive the physiological parameter from an information processing apparatus according to any one of claims 12 to 22 and in the event that the physiological parameter exceeds a threshold value, the server processing circuitry is configured to control the communication circuitry to issue an alert over a network.
24. A computer program comprising computer readable instructions which, when loaded onto a computer, configure the computer to perform a method according to any one of claims 1 to 11.

REFERENCES

[1] Roald N, "*Estimation of Vital Signs from Ambient-Light Non-Contact PPG*", 2013
[2] Lingqin Kong, Yuejin Zhao, Liquan Dong, Yiyun Jian, Xiaoli Jin, Bing Li, Yun Feng, Ming Liu, Xiaohua Liu and Hong Wu, "Non-Contact Detection of Oxygen Saturation based on Visible Light Imaging Device using Ambient Light", 2013

The invention claimed is:

1. A method of determining a physiological parameter of an individual, the method comprising the steps of:
   obtaining a series of images of a skin exposed region of the individual;
   performing a periodogram on at least one of the red, green and blue channels of the skin exposed region of the series of images to obtain frequency components of the channel;
   determining the physiological parameter based on the periodogram; and
   performing band pass filtering on the periodogram, the band pass filter being configured to pass through frequencies of the pulse of the individual.

2. A method according to claim 1, further comprising determining the power of each frequency component within the periodogram and determining the physiological parameter as the frequency component having the highest power within the periodogram.

3. A method according to claim 2, wherein the physiological parameter is the frequency component having the highest power at or below a threshold power.

4. A method according to claim 1, wherein the band pass filtering includes a plurality of bands and the method further comprises: determining the number of frequency components within each of the bands and determining the physiological parameter based on the number of frequency components within each of the bands.

5. A method according to claim 4, wherein the physiological parameter is a HRV and the HRV is calculated according to $$HRV = \frac{Number_{FirstFreq}}{Number_{SecondFreq}}$$

Where $Number_{FirstFreq}$ is the number of frequencies in a first frequency band and $Number_{SecondFreq}$ is the number of frequencies in a second frequency band, the frequency of the second frequency band being higher than the first frequency band.

6. A method according to claim 1, comprising applying a timestamp to each image in the series of images and providing a constant sample rate of images based on the applied timestamp.

7. A method according to claim 1 comprising converting each of the R, G, B signals into a Hue-Saturation-Value prior to performing the band-pass filtering.

8. An information processing apparatus for determining a physiological parameter of an individual, the apparatus comprising:
   image circuitry configured to obtain a series of images of a skin exposed region of the individual;
   processing circuitry configured to perform a periodogram on at least one of the red, green and blue channels of the skin exposed region of the series of images to obtain frequency components of the channel and to determine the physiological parameter based on the periodogram; and
   band pass filter circuitry configured to perform band pass filtering on the periodogram, the band pass filter circuitry being configured to pass through frequencies of the pulse of the individual.

9. An apparatus according to claim 8, wherein the processing circuitry is configured to determine the power of each frequency component within the periodogram and determine the physiological parameter as the frequency component having the highest power within the periodogram.

10. An apparatus according to claim 9, wherein the physiological parameter is the frequency component having the highest power at or below a threshold power.

11. An apparatus according to claim 9, wherein the band pass filter circuitry includes a plurality of bands and the processing circuitry is further configured to determine the number of frequency components within each of the bands and determining the physiological parameter based on the number of frequency components within each of the bands.

12. An apparatus according to claim 11, wherein the physiological parameter is a HRV and the HRV is calculated according to $$HRV = \frac{Number_{FirstFreq}}{Number_{SecondFreq}}$$

Where $Number_{FirstFreq}$ is the number of frequencies in a first frequency band and $Number_{SecondFreq}$ is the number of frequencies in a second frequency band, the frequency of the second frequency band being higher than the first frequency band.

13. An apparatus according to claim 8, wherein the processing circuitry is configured to apply a timestamp to each image in the series of images and providing a constant sample rate of images based on the applied timestamp.

14. A server comprising communication circuitry and server processing circuitry configured to receive the physiological parameter from an information processing apparatus according to claim 8 and in the event that the physiological parameter exceeds a threshold value, the server processing circuitry is configured to control the communication circuitry to issue an alert over a network.

15. A computer program comprising computer readable instructions which, when loaded onto a computer, configure the computer to perform a method according to claim 1.

* * * * *